United States Patent
Lui et al.

(10) Patent No.: US 8,450,528 B2
(45) Date of Patent: May 28, 2013

(54) PROCESS FOR THE PREPARATION OF 2,2-DIFLUOROETHYLAMINE STARTING FROM A BENZYLAMINE COMPOUND

(75) Inventors: Norbert Lui, Odenthal (DE); Jens-Dietmar Heinrich, Burscheid (DE); Christian Funke, Leichlingen (DE); Günter Schlegel, Leverkusen (DE); Thomas Norbert Müller, Monheim (DE)

(73) Assignee: Bayer Cropscience AG, Monheim (DE)

( * ) Notice: Subject to any disclaimer, the term of this patent is extended or adjusted under 35 U.S.C. 154(b) by 5 days.

(21) Appl. No.: 13/292,987

(22) Filed: Nov. 9, 2011

(65) Prior Publication Data

US 2012/0123163 A1  May 17, 2012

Related U.S. Application Data

(60) Provisional application No. 61/413,045, filed on Nov. 12, 2010.

(30) Foreign Application Priority Data

Nov. 12, 2010 (EP) .................................... 10191061

(51) Int. Cl.
C07C 209/00 (2006.01)
C07C 221/00 (2006.01)
C07C 223/00 (2006.01)
C07C 225/00 (2006.01)
C07C 213/00 (2006.01)
C07C 215/00 (2006.01)
C07C 217/00 (2006.01)
C07C 211/00 (2006.01)

(52) U.S. Cl.
USPC ........... 564/386; 564/343; 564/346; 564/374; 564/384; 564/336

(58) Field of Classification Search
None
See application file for complete search history.

(56) References Cited

U.S. PATENT DOCUMENTS

| | | | |
|---|---|---|---|
| 4,030,994 A | 6/1977 | Kollonitsch | |
| 8,106,211 B2 * | 1/2012 | Jeschke et al. | 546/279.7 |
| 8,324,393 B2 * | 12/2012 | Lui et al. | 546/329 |
| 2010/0274021 A1 | 10/2010 | Lui et al. | |

FOREIGN PATENT DOCUMENTS

| | | | |
|---|---|---|---|
| DE | 102006015467 | * | 10/2007 |
| WO | 2009036901 | | 3/2009 |

OTHER PUBLICATIONS

Koga, et al. Chem. Pharm. Bull 48(4) 571-574 (2000).*
European Search Report of EP 10 19 1061 dated Feb. 17, 2011, pp. 1-5.
Houben Weyl "B. Synthesis of Fluorinated Compounds," vol. E10, (2000) pp. 92-98.
J.B. Dickey et al. "Fluorinated Aminoanthraquinone Dyes," Industrial and Engineering Chemistry, vol. 48, No. 2. (1956), pp. 209-213. XP002559402.
Kluger et al., "Carboxylic Acid Participation in Amide Hydrolysis. Evidence That Separation of a Nonbonded Complex Can be Rate Determining", J. Am. Chem. Soc. (1982) vol. 104, pp. 2891-2897. XP-002504652.
Donetti et al. "N-(Fluoroethyl)(imidazoylphenyl)formamidines. The Issue of the Active Species of Mifentidine," J. Med. Chem. (1989) vol. 32, pp. 957-961. XP-002573225.
Verniest et al. "Synthesis and Reactivity of 1-Substituted 2-Fluoro- and 2,2-Difluoroaziridines," J. Org. Chem (2007) vol. 27, pp. 8569-8572. XP-002630131.
Hudlicky et al. "Chemistry of Organic Fluorine Compounds," Ellis Horwood Limited, (1976), pp. 489-495. XP-009146465.
Vyazkov et al. "Russia Fluorine Notes" (2009) vol. 65, No. 2. page 1.
Fred Swarts "Uber Einige Fluorhaltige-Alkylamine", Chem, Zentralblatt, (1904) vol. 75, pp. 944-945. XP-009126801.
Aoki et al. "Enantioselective Deprotonation of 4-tert-Butylcyclohexanone by Fluorine-Containing Chiral Lithium Amides Derived from a-Phenethylamine," Tetrahedron Letters, vol. 38, No. 14, (1997) pp. 2505-2506.
International Search Report of PCT/EP2011/069545 Dated February 8, 2012, pp. 1-3.

* cited by examiner

Primary Examiner — Sudhakar Katakam
Assistant Examiner — Clinton Brooks
(74) Attorney, Agent, or Firm — Baker Donelson Bearman Caldwell & Berkowitz, PC

(57) ABSTRACT

Process for the preparation of 2,2-difluoroethylamine of the formula (I)

$$CHF_2CH_2NH_2 \qquad (I)$$

comprising the stages (i) and (ii):
stage (i): reaction of 2,2-difluoro-1-haloethane of the general formula (II)

$$CHF_2-CH_2Hal \qquad (II),$$

with a benzylamine compound of the formula (III)

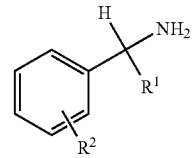

(III)

in the presence of an acid scavenger,
in which, in formula (II),
Hal is chlorine, bromine or iodine,
and, in the formulae (III),
$R^1$ is hydrogen or $C_1$-$C_{12}$-alkyl, and
$R^2$ is hydrogen, halogen, $C_1$-$C_{12}$-alkyl or $C_1$-$C_6$-alkoxy;
stage (ii): catalytic hydrogenation of the N-benzyl-2,2-difluoroethanamine compound obtained in the stage (i) to give 2,2-difluoroethylamine of the formula (I) or a salt thereof.

15 Claims, No Drawings

PROCESS FOR THE PREPARATION OF 2,2-DIFLUOROETHYLAMINE STARTING FROM A BENZYLAMINE COMPOUND

CROSS REFERENCE TO RELATED APPLICATIONS

This application claims priority to EP 10191061.0 filed Nov. 12, 2010 and U.S. Provisional Application No. 61/413,045 filed Nov. 12, 2010, the contents of both of which are hereby incorporated herein by reference in their entireties.

BACKGROUND

1. Field of the Invention

The present invention relates to a process for the preparation of 2,2-difluoroethylamine through the reaction of a benzylamine compound with 2,2-difluoro-1-haloethane.

2. Description of Related Art 2,2-Difluoroethylamine is an important intermediate in active substance preparation. Various methods for the preparation of 2,2-difluoroethylamine are known (e.g. WO2009/036901).

Donetti et al. (J. Med. Chem., 1989, 32, 957-961) describe the synthesis of 2,2-difluoroethylamine hydrochloride starting from 2,2-difluoroacetamide. On this occasion, the desired amine is prepared with a diborane solution in tetrahydrofuran (THF). The yield is 48%.

Kluger et al. (JACS, 1982, 104, 10, pages 2891-2897) describe the synthesis of 2,2-difluoroethylamine starting from the amide with sodium borohydride and boron trifluoride etherate. The yield is 60%. Vyazkov, V. A. et al. (Vyazkov, V. A., Gontar, A. F., Grinevskaya, V. K., Igoumnova, E. V. and Igoumnov, S. M., A. N. Nesmeyanov, Institute of Organoelement Compounds, Russian Academy of Sciences, Moscow, Russia Fluorine Notes (2009), 65) likewise describe the reduction with sodium borohydride in a yield of 50-65%.

In addition, Kollonitsch (U.S. Pat. No. 4,030,994) describes a synthesis of 2,2-difluoroethylamine, namely the reaction of ethylamine with fluoroxytrifluoromethane in hydrogen fluoride under UV radiation.

Swarts, in a paper with the title "Ober einige fluorhaltige Alkylamine" [On some fluorine-comprising alkylamines] (Chem. Zentralblatt, Volume 75, 1904, pages 944-945), describes the preparation of 2,2-difluoroethylamine and of tetrafluoroethylamine, with subsequent separation of the two products by fractional distillation or as hydrochloride or oxalate salts, after prior conversion of the products obtained. Swarts uses 1-bromo-2,2-difluoroethane as starting compound and heats this over a relatively long period of time, namely 3 days, in the reactor tube with 2 mol of alcoholic ammonia at relatively high temperatures, namely 125°-145° C. The starting compound is completely converted to the compounds difluoroethylamine and tetrafluoroethylamine.

The preparation of 2,2-difluoroethylamine is also described by Dickey et al. (Industrial and Engineering Chemistry, 1956, No. 2, 209-213). 2,2-Difluoro-1-chloroethane is there reacted with 28% ammonium hydroxide, i.e. 28% aqueous ammonia solution, in an autoclave (rocking autoclave). The reaction mixture is heated at temperatures of 135° to 140° C. for 31 hours. After the reaction has ended, the reaction mixture is filtered and amine is distilled off from the reaction mixture. Since, however, a lot of ammonia and some water still remain in the distillate, the amine is dried over sodium hydroxide and again distilled. The amine was thus obtained in a yield of 65%.

This process is disadvantageous as it requires—just as the process according to Swarts—a very long reaction time of 31 hours and the yield of 65% is rather low. At the same time, the reaction mixture is highly corrosive, since the aqueous ammonia, in combination with the chloride and fluoride ions present in the reaction mixture, attacks metallic materials at the high temperatures used in the process.

All these known processes are disadvantageous, in particular because they cannot be carried out on the commercial (industrial) scale which is useful economically. The low yields and the use of expensive and dangerous chemicals, such as, e.g., sodium borohydride/BF3 or diborane, prevent the processes according to Donetti et al. and Kluger et al. from being suitable for the commercial scale preparation of 2,2-difluoroethylamine. The process according to Kollonitsch et al. uses dangerous chemicals and pure 2,2-difluoroethylamine is not obtained. The process according to Dickey et al. and the process according to Swarts are likewise unsuitable or uneconomic for commercial scale use since they require very long reaction times and are at the same time nonselective, so that the yields of the processes are unsatisfactory.

Furthermore, the use of ammonia at high temperatures is problematic since special pressure-resistant equipment is necessary, which is demanding and expensive from a safety viewpoint.

Starting from the known processes for the preparation of 2,2-difluoroethylamine, the question now arises of how 2,2-difluoroethylamine can be prepared in a simple and inexpensive way. The term "inexpensive processes" is understood to mean those processes which can be carried out without major financial costs, because the starting materials, for example, are not dangerous, no other technical problems emerge, for example because the reaction mixture acts corrosively, and/or the desired 2,2-difluoroethylamine is obtained in a satisfactorily high yield and with a satisfactorily high purity, because, for instance, the reaction takes place to a great extent selectively.

SUMMARY

A particularly advantageous process for the preparation of 2,2-difluoroethylamine has now been found, in which the abovementioned disadvantages are avoided and which can be implemented in a simple way on the commercial scale. In the process according to the invention, in a first stage, a 2,2-difluoro-1-haloethane compound is selectively converted to the desired N-benzyl-2,2-difluoroethanamine compound under comparatively mild reaction conditions and in a comparatively short reaction time. In a second stage, the benzyl group is again removed by catalytic hydrogenation and the desired N,N-difluoroethylamine correspondingly obtained.

A subject-matter of the invention is accordingly a process for the preparation of 2,2-difluoroethylamine of the formula (I)

$$CHF_2CH_2NH_2 \qquad (I)$$

which comprises the following stages (i) and (ii):
stage (i)—alkylation: reaction of 2,2-difluoro-1-haloethane of the general formula (II)

$$CHF_2\text{—}CH_2Hal \qquad (II),$$

in which Hal is chlorine, bromine or iodine; Hal is preferably chlorine or bromine, very preferably chlorine,
with a benzylamine compound of the formula (III)

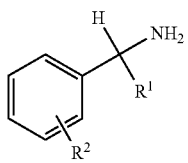
(III)

in which:

R$^1$ is hydrogen or C$_1$-C$_{12}$-alkyl; preferably, R$^1$ is hydrogen or C$_1$-C$_6$-alkyl, and R$^2$ is hydrogen, halogen, C$_1$-C$_{12}$-alkyl or C$_1$-C$_6$-alkoxy; preferably, R$^2$ is hydrogen, fluorine, chlorine, C$_1$-C$_6$-alkyl or C$_1$-C$_3$-alkoxy (in particular methoxy), to give an N-benzyl-2,2-difluoroethanamine compound of the formula (IV)

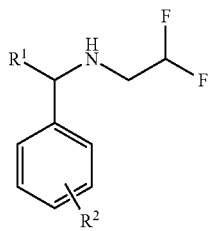
(IV)

in which R$^1$ and R$^2$ are as defined above, in the presence of an acid scavenger, i.e. a compound which is able to inactivate (neutralize) an acid;

and stage (ii): catalytic hydrogenation of the N-benzyl-2,2-difluoroethanamine compound of the formula (IV) obtained in stage (i) to give 2,2-difluoroethylamine of the formula (I) or a salt thereof.

DETAILED DESCRIPTION OF A PREFERRED EMBODIMENT

The process according to the invention can be illustrated by the following scheme:

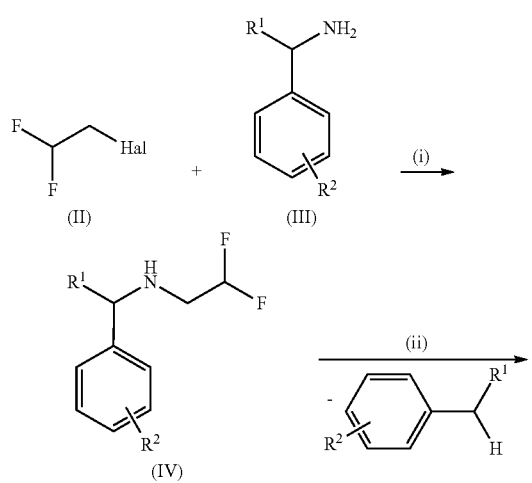

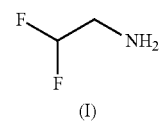
(I)

The desired 2,2-difluoroethylamine is obtained, by the process according to the invention, with good yields, with short reaction times and in high purity, which is why it is generally not necessary to extensively rework the actual reaction product.

A subject-matter of the invention is likewise the process of the stage (i) for the preparation of N-benzyl-2,2-difluoroethanamine of the formula (IV)

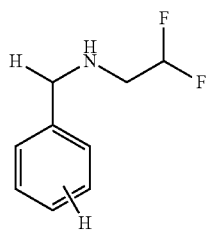
(IV)

comprising the reaction of 2,2-difluoro-1-chloroethane with benzylamine of the formula (III)

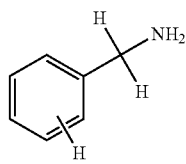
(III)

in the presence of an acid scavenger, which comprises the process stages, reaction conditions and reactants described for stage (i).

A subject-matter of the invention is furthermore the use of benzyl-2,2-difluoroethanamine of the formula (IV) in the preparation of 2,2-difluoroethylamine, which comprises the process stages, reaction conditions and reactants described for stage (ii).

Although it is known, from M. Hudlicky in "Chemistry of Organofluorine Compounds", 2nd edition, 1976, pp. 489-490, and Houben Weyl, E 10b/2, pp. 92-98, that 2,2-difluoro-1-haloethane reacts under basic conditions with elimination of HHal (HCl, HBr or HI) to give vinylidene fluoride and is accordingly no longer available for the reaction in stage (i) and although it is known, from J. Org. Chem., 2007, 72 (22), pp. 8569, that 2,2-difluoroethylamines are very reactive and it is highly probable that the N-benzyl-2,2-difluoroethanamine compound of the formula (IV) obtained will react further under the reaction conditions in the stage (i), the inventors have found, surprisingly, that the N-benzyl-2,2-difluoroethanamine compound of the formula (IV) is obtained by stage (i) of the process according to the invention in a good yield and with a good purity, so that an extensive purification can be dispensed with. At the end of the day, the target compound 2,2-difluoroethylamine is accordingly also obtained in a very good yield, based on the starting materials used in the stage (i).

With regard to the alkylation in the stage (i), the inventors have found, contrary to the expectation that increased double or multiple alkylations will occur, that, if the sum of the molar amounts of benzylamine compound of the formula (III) to be reacted and acid scavenger is less than the molar amount of 2,2-difluorohaloethane of the formula (II) used, very high yields are achieved. If the benzylamine compound of the formula (III) is used both as starting material and as acid scavenger, it also applies here that the sum of the molar amount of benzylamine compound of the formula (III) which is reacted and the molar amount of benzylamine compound of the formula (III) which acts as acid scavenger is lower than the molar amount of 2,2-difluorohaloethane of the formula (II) used.

In the process according to the invention, use is preferably made of 2,2-difluoro-1-haloethane compounds of the formula (II) in which Hal is chlorine or bromine. Use is particularly preferably made of the compound 2,2-difluoro-1-chloroethane ($CHF_2$—$CH_2Cl$).

In the process according to the invention, use is furthermore preferably made of benzylamine compounds of the formula (III) in which
  (a) $R^1$ is chosen from a group consisting of hydrogen, methyl, ethyl, n-propyl and isopropyl and in which $R^2$ is chosen from the group consisting of hydrogen, methyl, chlorine and methoxy; or
  (b) $R^1$ is chosen from a group consisting of hydrogen and methyl and $R^2$ is chosen from a group consisting of hydrogen, methyl and chlorine; or
  (c) $R^1$ and $R^2$ are each hydrogen.

Benzylamine compounds of the formula (III) are known. They can be prepared according to known processes and are in some cases also available commercially.

It is particularly preferable to react, in the process according to the invention, 2,2-difluoro-1-chloroethane, as compound of the formula (II), with a benzylamine compound of the formula (III) in which the R1 and R2 radicals have the meanings mentioned under one of the points (a), (b) or (c).

Unless otherwise indicated, the expression "alkyl", in isolation or in combination with other terms, such as, for example, alkoxy, refers to linear or branched saturated hydrocarbon chains with up to 12 carbon atoms, i.e. C1-C12-alkyl, preferably with up to 6 carbons, i.e. C1-C6-alkyl, particularly preferably with up to 4 carbons, i.e. C1-C4-alkyl. Examples of such alkyls are methyl, ethyl, n-propyl or isopropyl, n-, iso-, s- or t-butyl, n-pentyl, n-hexyl, n-heptyl, n-octyl, n-nonyl, n-decyl, n-undecyl and n-dodecyl. The alkyls can be substituted with a suitable substituent, e.g. with halogen.

Unless otherwise indicated, "halogen" or "Hal" is fluorine, chlorine, bromine or iodine.

The reaction of 2,2-difluoro-1-haloethane of the formula (II) with the benzylamine compound of the formula (III) from stage (i) can be carried out neat, i.e. without addition of a solvent, or in the presence of a solvent.

In the case of a solvent being added to the reaction mixture in stage (i), it is preferably used in such an amount that the reaction mixture remains satisfactorily stirrable during the whole process. Use is advantageously made, based on the volume of the 2,2-difluoro-1-haloethane used, of the solvent in an amount of 1 to 50 times, preferably 2 to 40 times and particularly preferably 2 to 20 times. The term "solvent" is also understood to mean, according to the invention, mixtures of pure solvents. Suitable solvents are all organic solvents which are inert under the reaction conditions. Suitable solvents according to the invention are in particular water, ethers (e.g. ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, 2-methyltetrahydrofuran, dioxane, and ethylene oxide and/or propylene oxide polyethers); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide or diisoamyl sulphoxide; sulphones, such as dimethyl, diethyl, dipropyl, dibutyl, diphenyl, dihexyl, methyl ethyl, ethyl propyl, ethyl isobutyl and pentamethylene sulphone; aliphatic, cyclooaliphatic or aromatic hydrocarbons (e.g. pentane, hexane, heptane, octane, nonane, such as white spirits with components with boiling points in the range, for example, from 40° C. to 250° C., cymene, benzine fractions within a boiling point interval from 70° C. to 190° C., cyclohexane, methylcyclohexane, petroleum ether, ligroin, benzene, toluene or xylene); halogenated aromatic compounds (e.g. chlorobenzene or dichlorobenzene); amides (e.g. hexamethylphosphoramide, formamide, N,N-dimethylacetamide, N-methyl-formamide N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine or N,N'-1,4-diformylpiperazine); nitriles (e.g. acetonitrile, propionitrile, n-butyronitrile, isobutyronitrile or benzo-nitrile); ketones (e.g. acetone) or mixtures thereof.

Preferred solvents in stage (i) are aromatic and/or aliphatic hydrocarbons, in particular toluene, N,N-dimethylacetamide, tetramethylene sulphoxide and N-methylpyrrolidone.

It is preferred, according to the invention, to carry out stage (i) neat, i.e. without solvent. The process can through this be carried out even more inexpensively, because the solvent neither has to be purchased nor disposed of after reaction.

The reaction of the stage (i) is advantageously carried out in the presence of one or more acid scavengers which are able to bind the hydrogen halide compounds (i.e. HCl, HBr or HI) released in the reaction.

Suitable acid scavengers are all organic and inorganic bases which are able to bind the hydrogen halide compounds released. Examples of organic bases are tertiary nitrogen bases, such as, e.g., tertiary amines, substituted or unsubstituted pyridines and substituted or unsubstituted quinolines, triethylamine, trimethylamine, diisopropylethylamine, tri-n-propylamine, tri-n-butylamine, tri-n-hexylamine, tricyclohexylamine, N-methyl-cyclohexylamine, N-methylpyrrolidine, N-methylpiperidine, N-ethylpiperidine, N,N-dimethylaniline, N-methylmorpholine, pyridine, 2-, 3- or 4-picoline, 2-methyl-5-ethylpyridine, 2,6-lutidine, 2,4,6-collidine, 4-dimethylaminopyridine, quinoline, quinaldine, N,N,N,N-tetramethylethylenediamine, N,N-dimethyl-1,4-diazacyclohexane, N,N-diethyl-1,4-diazacyclohexane, 1,8-bis(dimethylamino)naphthalene, diazabicyclooctane (DABCO), diazabicyclononane (DBN), diazabicycloundecane (DBU), butylimidazole and methylimidazole.

Examples of inorganic bases are alkali metal or alkaline earth metal hydroxides, hydrogencarbonates or carbonates and other inorganic aqueous bases; preference is given, e.g., to sodium hydroxide, potassium hydroxide, lithium hydroxide, calcium hydroxide, sodium carbonate, potassium carbonate, sodium hydrogencarbonate, potassium hydrogencarbonate and sodium acetate.

The molar ratio of acid scavenger, in particular of above-mentioned bases, to benzylamine compound of the formula (III) used lies in the range from approximately 0.1 to approximately 3, preferably in the range from approximately 0.5 to approximately 3, particularly preferably in the range from approximately 0.7 to approximately 1.3. The use of larger amounts of base is technically possible but results, however, in a fall in yield.

The molar ratio of 2,2-difluoro-1-haloethane to the amine of the formula (III) used normally lies in the range from approximately 30:1 to approximately 1:3, preferably in the range from approximately 10:1 to approximately 1:2 and particularly preferably in the range from approximately 8:1 to approximately 1:1.

In a preferred embodiment, the benzylamine compound of the formula (III) is used as acid scavenger, so that no additional acid scavenger has to be used. In this case, the molar ratio of 2,2-difluoro-1-haloethane to the amine of the formula (III) used normally lies in the range from approximately 15:1 to approximately 1:3, preferably in the range from approximately 8:1 to approximately 1:2.5 and particularly preferably in the range from approximately 4:1 to approximately 1:2.

The benzylamine compound of the formula (III) and the base can also be introduced into the 2,2-difluoro-1-halo ethane of the formula (II).

Although stage (i) of the process according to the invention is generally carried out without addition of a catalyst, catalysts which accelerate the reaction of a benzylamine compound of the formula (III) with 2,2-difluorohaloethane can also be used in the stage (i). The reaction temperature is lowered by the use of a catalyst, which also results in the lowering of the intrinsic pressure of the reaction mixture. If the intrinsic pressure is not so high, the operation can be carried out under simpler conditions industrially.

Suitable according to the invention are in particular alkali metal bromides and iodides (e.g. sodium iodide, potassium iodide or potassium bromide); ammonium bromide and ammonium iodide; tetraalkylammonium bromides and iodides (e.g. tetraethylammonium iodide); certain phosphonium halides, such as tetraalkyl- or tetraarylphosphonium halides (e.g. hexadecyl(tributyl)phosphonium bromide, stearyltributylphosphonium bromide, tetrabutylphosphonium bromide, tetraoctylphosphonium bromide, tetraphenylphosphonium chloride and tetraphenylphosphonium bromide), tetrakis(dimethylamino)phosphonium bromide, tetrakis(diethylamino)phosphonium bromide, tetrakis(dipropylamino)phosphonium chloride and bromide; and bis(dimethylamino)[(1,3-dimethylimidazolidin-2-ylidene)amino] methylium bromide. In addition, mixtures of suitable catalysts are also conceivable.

Of the abovementioned catalysts, sodium iodide, potassium iodide, potassium bromide, tetrabutylammonium bromide and tetraphenylphosphonium bromide are particularly suitable for accelerating the reaction of the stage (i). Sodium iodide and potassium iodide are to be particularly emphasized.

The catalyst can also be produced in situ, for example be produced by a reaction of HBr or HI with ammonia or by addition of highly reactive alkyl bromides or iodides (e.g. methyl bromide, ethyl bromide, methyl iodide or ethyl iodide).

If a catalyst is present in the stage (i), it is used, based on the 2,2-difluoro-1-haloethane of the formula (II) used, in a concentration of approximately 0.01 to approximately 25% by weight. Higher concentrations are possible in principle. The catalyst is preferably used in a concentration of approximately 0.2 to approximately 25% by weight, particularly preferably of approximately 0.4 to approximately 20% by weight and very particularly preferably of approximately 0.5 to approximately 15% by weight. However, the catalyst can also preferably be used in a concentration of approximately 0.05 to approximately 3% by weight, of approximately 0.1 to approximately 10% by weight or of approximately 0.5 to approximately 10% by weight.

The reaction of the stage (i) is carried out in principle under intrinsic pressure in a pressure-resistant closed test vessel (autoclave). The pressure during the reaction (i.e., the intrinsic pressure) depends on the reaction temperature used, the 2,2-difluoro-1-haloethane used, the catalyst used and the amount of benzylamine compound of the formula (III) used. The pressure likewise also depends on the solvent used, if a solvent is present in the stage (i). If an increase in pressure is desired, an additional increase in pressure can be achieved by addition of inert gas, such as nitrogen or argon.

The reaction temperature in stage (i) can vary depending on the starting materials used. If a catalyst is not added in the stage (i), stage (i) is carried out at internal temperatures (i.e., the temperature present in the reaction vessel) in the range from approximately 70° C. to approximately 200° C. It is preferable, in carrying out the reaction stage (i), for the internal temperature to lie in the range from approximately 90° C. to approximately 150° C., particularly preferably in the range from approximately 90° C. to approximately 140° C. It has been established that, if the operation is carried out in the preferred temperature range, few side reactions, in particular multiple alkylations, occur.

If a catalyst is used in stage (i), the reaction temperature of the reaction mixture is correspondingly reduced. A person skilled in the art knows to what extent the reaction temperature is lowered on addition of a certain catalyst and he can, from routine experiments or from his knowledge and from the abovementioned internal temperature ranges, find the optimum reaction internal temperature range for the specific reaction mixture.

The reaction time of the reaction in stage (i) is short and lies in the range from approximately 0.5 to approximately 20 hours. A longer reaction time is possible but is not useful economically.

The reaction mixture from stage (i) is worked up either by filtration and subsequent fractional distillation or by diluting (addition of water in which possible salts are dissolved) the reaction mixture and subsequent phase separation, followed by fractional distillation. The base or the benzylamine compound of the formula (III) can be rereleased by liberation with an additional base, e.g. sodium hydroxide solution, and can be accordingly fed back again into the process.

The N-benzyl-2,2-difluoroethanamine compound of the formula (IV) is then subjected to the catalytic hydrogenation of the stage (ii).

In the catalytic hydrogenation of the N-benzyl-2,2-difluoroethanamine compound of the formula (IV) to give the 2,2-difluoroethylamine of the formula (I) in stage (ii), gaseous hydrogen is introduced into the reaction vessel or is produced in situ in the reaction vessel by the use of formic acid or hydrazine and the derivatives thereof or salts thereof.

Use may be made, as catalyst for the catalytic hydrogenation according to stage (ii), of any suitable catalyst for catalytic hydrogenation known to a person skilled in the art. Palladium catalysts, platinum catalysts, Raney nickel catalysts or Raney cobalt catalysts, Lindlar catalysts, ruthenium catalysts and rhodium catalysts are possible, for example. In addition to these heterogeneous catalysts, homogeneous catalysts can also be used. Suitable catalysts preferably comprise one or more metals from Groups 8-10 of the Periodic Table, in particular one or more metals chosen from iron, ruthenium, osmium, cobalt, rhodium, iridium, nickel, palladium and platinum. The metals can be present in any chemical form, e.g. elemental, colloidal, as salts or oxides, together with complexing agents as chelates, or as alloys, in which the alloys can also comprise, in addition to the metals listed above, other metals, such as, for example, aluminium. The metals can be present in supported form, i.e. applied to any support, preferably an inorganic support. Carbon (graphite, charcoal or active charcoal), aluminum oxide, silicon dioxide, zirconium dioxide, calcium carbonate, barium sulphate and titanium dioxide are suitable, for example, as carriers. Preferred catalysts according to the invention comprise one or more metals from Groups 8-10 of the Periodic Table on an inorganic carrier. Particular preference is given according to the invention to catalysts which comprise platinum and/or palladium and which may be applied to an inorganic carrier. Such catalysts are, for example, $PtO_2$, $Pd(OH)_2$ on active charcoal (Pearlman's catalyst), Raney nickel catalysts and Lindlar catalysts. The catalysts can be used both in their water-moistened form and in their dry form. The catalyst used is preferably reused for several reactions.

The catalyst is used in the process according to the invention, based on the N-benzyl-2,2-difluoroethanamine compound of the formula (IV) used, in a concentration of approximately 0.01 to approximately 30% by weight. The catalyst is preferably used in a concentration of approximately 0.1 to approximately 12% by weight, preferably of approximately 0.1 to approximately 2.5% by weight.

The catalytic hydrogenation of stage (ii) is carried out neat or in a suitable solvent. If stage (ii) is carried out in a solvent, the solvent is also here preferably used in such an amount that the reaction mixture remains stirrable during the whole process. Use is advantageously made, based on the N-benzyl-2,2-difluoroethanamine compound of the formula (IV) used, of the solvent in an amount of approximately 1 to 50 times (v/v), preferably approximately 2 to 40 times and particularly preferably 2 to 10 times.

All organic solvents which are inert under the reaction conditions are suitable as solvent. The term "solvent" is also understood to mean, according to the invention, mixtures of pure solvents.

Solvents suitable according to the invention in the stage (ii) are in particular water, ethers (e.g. ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, 2-methyltetrahydrofuran, dioxane, and ethylene oxide and/or propylene oxide polyethers); aliphatic, cycloaliphatic or aromatic hydrocarbons (e.g. pentane, hexane, heptane, octane, nonane, such as the white spirits with components with boiling points in the range, for example, from 40° C. to 250° C., cymene, benzine fractions within a boiling point interval from 70° C. to 190° C., cyclohexane, methylcyclohexane, petroleum ether, ligroin, octane, benzene, toluene or xylene); linear and branched carboxylic acids (e.g. formic acid, acetic acid, propionic acid, butyric acid and isobutyric acid) and their esters (e.g. ethyl acetate and butyl acetate), alcohols (e.g. methanol, ethanol, isopropanol, n-butanol and isobutanol) or mixtures thereof.

Preference is given to aromatic or aliphatic hydrocarbons, in particular toluene and xylene, methanol, acetic acid and n-butyl acetate.

An organic or inorganic acid can be added in the stage (ii) to accelerate the catalytic hydrogenation. Examples of organic acids are aliphatic unbranched and branched mono-, di- and tricarboxylic acids (e.g. acetic acid, isobutyric acid, oxalic acid, citric acid and trifluoroacetic acid); sulphonic acid derivatives (e.g. p-toluenesulphonic acid, p-chlorosulphonic acid, methanesulphonic acid and trifluoromethanesulphonic acid). Examples of inorganic acids are hydrochloric acid, hydrobromic acid, sulphuric acid and phosphoric acid.

The molar ratio of acid to N-benzyl-2,2-difluoroethanamine compound of the formula (IV) used lies in the range from approximately 0.001 to approximately 10, preferably in the range from approximately 0.01 to approximately 5 and particularly preferably in the range from approximately 0.02 to approximately 1. The use of larger amounts of acid is possible in principle. With suitable ability to be handled, the acid can also be used as solvent.

The catalytic hydrogenation in stage (ii) can be carried out at temperatures in the range from approximately 0° C. to approximately 200° C. Preferably, the internal temperature lies in the range from approximately 20° C. to approximately 150° C.; it lies particularly preferably in the range from approximately 40° C. to 130° C.

The reaction time of the catalytic hydrogenation is short and lies in the range from approximately 0.1 to 12 hours. A longer reaction time is possible but is not useful economically.

The catalytic hydrogenation can be carried out under excess pressure (i.e., up to approximately 200 bar) in an autoclave or at standard pressure in a hydrogen gas atmosphere. With high reaction temperatures in particular, it can be helpful to operate at elevated pressure. The (additional) increase in pressure can be brought about by supplying an inert gas, such as nitrogen or argon. The hydrogenation according to the invention is preferably carried out at a pressure in the range from approximately 1 to approximately 100 bar, particularly preferably at a pressure in the range from approximately 1.5 to approximately 10 bar.

The catalytic hydrogenation can take place as pump hydrogenation or in the batch process. In the pump hydrogenation, the N-benzyl-2,2-difluoroethanamine compound of the formula (IV), which is dissolved in the solvents described above or is present neat, is added continuously, and in the batch process portionwise, to an autoclave. The autoclave is under a hydrogen atmosphere and is charged with at least one of the abovementioned catalysts.

After the end of the reaction, the 2,2-difluoroethylamine of the formula (I) obtained can be purified by distillation. Alternatively, the 2,2-difluoroethylamine of the formula (I) can also be isolated and purified as salt, e.g. hydrochloride. The salt is produced, before, during or after the catalytic hydrogenation, by addition of acid. The salt can subsequently be rereleased by addition of base.

The 2,2-difluoroethylamine of the formula (I) is commonly present, after the reaction according to the invention, in such a purity that it can be used further in the solvent after filtration of the catalyst.

The present invention is more fully described from the following examples, without the invention in this connection being limited to these.

PREPARATION EXAMPLES

Example 1

Preparation of N-benzyl-2,2-difluoroethanamine (Stage (i))

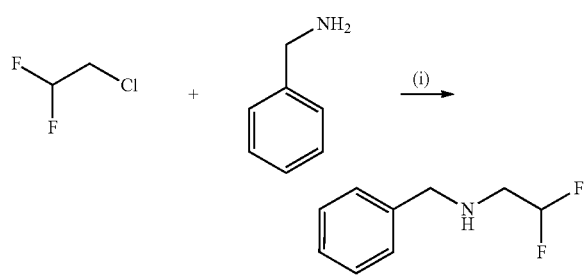

Example 1.1

An amount of 1152 g (11.1 mol) of 2,2-difluoro-1-chloroethane and 403 g of benzylamine (3.695 mol) are heated in an autoclave at an internal temperature of 120° C. for 16 hours. Subsequently, 700 g of water are added and the aqueous phase is separated. The aqueous phase comprises benzylamine hydrochloride, which is converted back into free benzylamine by addition of sodium hydroxide solution. The organic phase is first distilled at standard pressure, the unreacted 2,2-difluoro-1-chloroethane being distilled off. Vacuum distillation is then again carried out (at approximately 200 mbar), the remaining traces of 2,2-difluoro-1-chloroethane being distilled off. An amount of 306 g of N-benzyl-2,2-difluoroethanamine is obtained as distillation residue with a purity of 98.9%. This corresponds to a yield of 95.6%, based on the benzylamine reacted. It is possible, by renewed distillation, to obtain N-benzyl-2,2-difluoroethanamine in a purity of greater than 99%.

$^1$H NMR (CDCl$_3$): 7.24-7.35 (m, 5H), 5.84 (tt, 1H), 3.84 (s, 2H), 2.95 (dt, 2H)

Example 1.2

An amount of 2 g (20 mmol) of 2,2-difluoro-1-chloroethane and 4.5 g (41 mmol) of benzylamine are heated in 62 g of N-methylpyrrolidone in an autoclave at an internal temperature of 120° C. for 16 hours. Subsequently, 50 g of 1N hydrochloric acid are added and the solvent is removed under vacuum. The residue is taken up in 50 ml of water and 50 ml of dichloromethane and adjusted to pH 8 with solid sodium hydrogencarbonate. The phases are subsequently separated and the aqueous phase is again extracted with 20 ml of dichloromethane. The organic phase is distilled. An amount of 2.4 g of N-benzyl-2,2-difluoroethanamine is obtained, which corresponds to a yield of 66.2%, based on 2,2-difluoro-1-chloroethane used.

$^1$H NMR (CDCl$_3$): 7.24-7.35 (m, 5H), 5.84 (tt, 1H), 3.84 (s, 2H), 2.95 (dt, 2H)

Example 1.3

An amount of 5 g (49.7 mmol) of 2,2-difluoro-1-chloroethane and 11.3 g (105 mmol) of benzylamine are heated in an autoclave at an internal temperature of 120° C. for 16 hours. Subsequently, 100 g of 1N hydrochloric acid are added and the solvent is removed under vacuum. The residue is taken up in 50 ml of water and 50 ml of dichloromethane and adjusted to pH 8 with solid sodium hydrogencarbonate. The phases are subsequently separated and the aqueous phase is again extracted with 20 ml of dichloromethane. The organic phase is distilled. An amount of 3.5 g of N-benzyl-2,2-difluoroethanamine is obtained, which corresponds to a yield of 41%, based on 2,2-difluoro-1-chloroethane used.

$^1$H NMR (CDCl$_3$): 7.24-7.35 (m, 5H), 5.84 (tt, 1H), 3.84 (s, 2H), 2.95 (dt, 2H)

Example 1.4

An amount of 10 g (92 mmol) of 2,2-difluoro-1-chloroethane, 5 g (46 mmol) of benzylamine and 5.2 g (51 mmol) of triethylamine are heated in 18.7 g of N,N-dimethylacetamide in an autoclave at an internal temperature of 120° C. for 6 hours. Subsequently, 100 g of 1N hydrochloric acid are added and the solvent is removed under vacuum. The residue is taken up in 30 ml of dichloromethane and adjusted to pH 8 with solid sodium hydrogencarbonate. The phases are subsequently separated and the aqueous phase is again extracted with 20 ml of dichloromethane. The organic phase is distilled. An amount of 7.1 g of N-benzyl-2,2-difluoroethanamine is obtained, which corresponds to a yield of 90%, based on benzylamine

Example 1.5

An amount of 10 g (92 mmol) of 2,2-difluoro-1-chloroethane, 5 g (46 mmol) of benzylamine and 5.2 g (51 mmol) of triethylamine are heated in 20.6 g of N-methylpyrrolidone in an autoclave at an internal temperature of 120° C. for 6 hours. Subsequently, 100 g of 1N hydrochloric acid are added and the solvent is removed under vacuum. The residue is taken up in 30 ml of dichloromethane and adjusted to pH 8 with solid sodium hydrogencarbonate. The phases are subsequently separated and the aqueous phase is again extracted with 20 ml of dichloromethane. The organic phase is distilled. An amount of 7.3 g of N-benzyl-2,2-difluoroethanamine is obtained, which corresponds to a yield of 93%, based on benzylamine.

$^1$H NMR (CDCl$_3$): 7.24-7.35 (m, 5H), 5.84 (tt, 1H), 3.84 (s, 2H), 2.95 (dt, 2H)

Example 1.6

An amount of 10 g (92 mmol) of 2,2-difluoro-1-chloroethane, 5 g (46 mmol) of benzylamine, 1 g of potassium bromide and 5.2 g (51 mmol) of triethylamine are heated in 20.6 g of N-methylpyrrolidone in an autoclave at an internal temperature of 120° C. for 6 hours. Subsequently, 100 g of 1N hydrochloric acid are added and the solvent is removed under vacuum. The residue is taken up in 30 ml of dichloromethane and adjusted to pH 8 with solid sodium hydrogencarbonate. The phases are subsequently separated and the aqueous phase is again extracted with 20 ml of dichloromethane. The organic phase is distilled. An amount of 7.4 g of N-benzyl-2,2-difluoroethanamine is obtained, which corresponds to a yield of 94%, based on benzylamine.

$^1$H NMR (CDCl$_3$): 7.24-7.35 (m, 5H), 5.84 (tt, 1H), 3.84 (s, 2H), 2.95 (dt, 2H)

Example 1.7

As Example 1.6. In place of 1 g of potassium bromide, 1.5 g of potassium iodide are used. N-Benzyl-2,2-difluoroethanamine is obtained in a yield of 95%, based on benzylamine.

$^1$H NMR (CDCl$_3$): 7.24-7.35 (m, 5H), 5.84 (tt, 1H), 3.84 (s, 2H), 2.95 (dt, 2H)

Example 1.8

An amount of 10 g (92 mmol) of 2,2-difluoro-1-chloroethane, 5 g (46 mmol) of benzylamine and 5.2 g (51 mmol) of triethylamine are heated in 20 g of water in an autoclave at an internal temperature of 120° C. for 6 hours. The two-phase solution is twice extracted with 50 ml of dichloromethane each time and the combined organic phases are washed with 50 ml of water and subsequently distilled. An amount of 5.2 g of N-benzyl-2,2-difluoroethanamine is obtained, which corresponds to a yield of 66%, based on benzylamine.

$^1$H NMR (CDCl$_3$): 7.24-7.35 (m, 5H), 5.84 (tt, 1H), 3.84 (s, 2H), 2.95 (dt, 2H)

Example 1.9

As Example 1.5. The reaction mixture is heated at an internal temperature of 140° C. for 6 h. N-Benzyl-2,2-difluoroethanamine is obtained in a yield of 83%, based on benzylamine.

$^1$H NMR (CDCl$_3$): 7.24-7.35 (m, 5H), 5.84 (tt, 1H), 3.84 (s, 2H), 2.95 (dt, 2H)

The dialkylated derivative N-benzyl-N-(2,2-difluoroethyl)-2,2-difluoroethanamine is isolated as secondary component.

$^1$H NMR (CDCl$_3$): 7.25-7.37 (m, 5H), 5.73 (tt, 2H), 3.86 (s, 2H), 3.0 (dt, 4H)

Example 1.10

An amount of 768.1 g (7.39 mol) of 2,2-difluoro-1-chloroethane and 400 g of benzylamine (3.695 mol) are heated in an autoclave at an internal temperature of 120° C. for 16 hours. Subsequently, 700 g of water are added and the aqueous phase is separated. The organic phase is distilled at standard pressure and the excess 2,2-difluoro-1-chloroethane is distilled off. Remaining traces of 2,2-difluoro-1-chloroethane are distilled off under vacuum (200 mbar). An amount of 304 g of N-benzyl-2,2-difluoroethanamine is obtained as residue with a purity of 97.2%. This corresponds to a yield of 93.4%, based on reacted benzylamine. The benzylamine hydrochloride in the aqueous phase can be rereleased by addition of sodium hydroxide solution and be used once again.

$^1$H NMR (CDCl$_3$): 7.24-7.35 (m, 5H), 5.84 (tt, 1H), 3.84 (s, 2H), 2.95 (dt, 2H)

Example 1.11

An amount of 757.9 g (7.39 mol) of 2,2-difluoro-1-chloroethane and 800 g of benzylamine (7.39 mol) are heated in an autoclave at an internal temperature of 120° C. for 16 hours. Subsequently, 1400 g of water are added and the aqueous phase is separated. The organic phase is distilled at standard pressure and the excess 2,2-difluoro-1-chlorethan is distilled off Remaining traces of 2,2-difluoro-1-chloroethane are distilled off under vacuum (200 mbar). An amount of 587 g of N-benzyl-2,2-difluoroethanamine is obtained as residue with a purity of 97.4%. This corresponds to a yield of 93.4%, based on reacted benzylamine. The benzylamine hydrochloride in the aqueous phase can be rereleased by addition of sodium hydroxide solution and be used once again. A further 21 g of N-benzyl-2,2-difluoroethanamine are present in the aqueous phase so that the yield is increased to 96%.

$^1$H NMR (CDCl$_3$): 7.24-7.35 (m, 5H), 5.84 (tt, 1H), 3.84 (s, 2H), 2.95 (dt, 2H)

Example 2

Preparation of
2,2-difluoro-N-(4-methylbenzyl)ethanamine
(Stage (i))

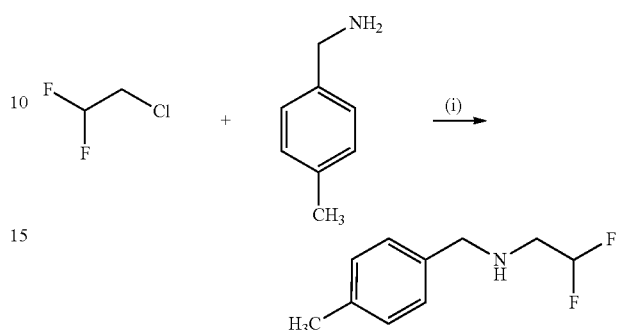

An amount of 26.2 g (242 mmol) of 2,2-difluoro-1-chloroethane and 10 g of 4-methylbenzylamine (80.8 mmol) are heated in an autoclave at an internal temperature of 120° C. for 16 hours. Subsequently, 50 g of water are added and the aqueous phase is separated. The aqueous phase is again extracted with 2,2-difluoro-1-chloroethane and the combined organic phases are distilled as described in Example 1.1. Here also, the 4-methylbenzylamine hydrochloride which is present in the aqueous phase can be converted back into free 4-methylbenzylamine by addition of sodium hydroxide solution. After distillation, 4.3 g of 2,2-difluoro-N-(4-methylbenzyl)ethanamine are obtained, which corresponds to a yield of 58%, based on reacted 4-methylbenzylamine.

$^1$H NMR (CDCl$_3$): 7.18 (d, 2H), 7.13 (d, 2H), 5.82 (tt, 1H), 3.78 (s, 2H), 2.93 (dt, 2H), 2.32 (s, 3H)

Example 3

Preparation of
2,2-difluoro-N-(4-chlorobenzyl)ethanamine
(Stage (i))

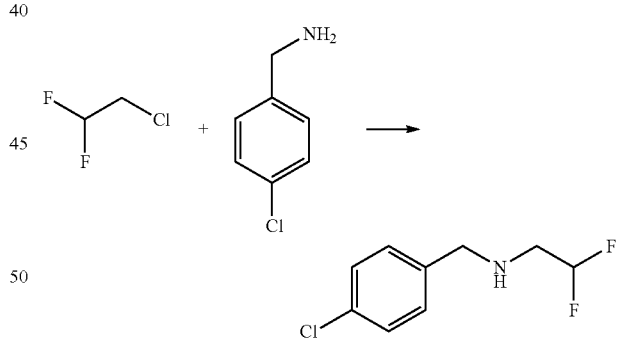

An amount of 22.4 g (207 mmol) of 2,2-difluoro-1-chloroethane and 10 g (69 mmol) of 4-chlorobenzylamine are heated in an autoclave at an internal temperature of 120° C. for 16 hours. Subsequently, 50 g of water are added and the aqueous phase is separated. The aqueous phase is again extracted with 2,2-difluoro-1-chloroethane and the combined organic phases are distilled as described in Example 1.1. Here also, the 4-chlorobenzylamine hydrochloride which is present in the aqueous phase can be converted back into free 4-chlorobenzylamine by addition of sodium hydroxide solution. After distillation, 4.25 g of 2,2-difluoro-N-(4-chlorobenzyl)ethanamine are obtained, which corresponds to a yield of 61%, based on reacted 4-chlorobenzylamine $^1$H NMR (CDCl$_3$): 7.24-7.3 (m, 4H), 5.84 (tt, 1H), 3.81 (s, 2H), 2.94 (dt, 2H)

Example 4

Preparation of 2,2-difluoro-N-(4-methoxybenzyl)ethanamine (Stage (i))

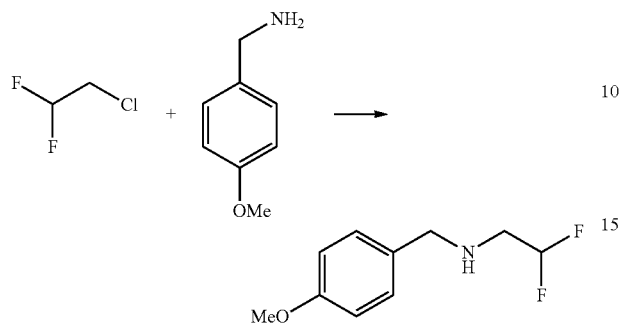

An amount of 23.15 g (214 mmol) of 2,2-difluoro-1-chloroethane and 10 g (71 mmol) of 4-methoxybenzylamine are heated in an autoclave at an internal temperature of 120° C. for 16 hours. Subsequently, 50 g of water are added and the aqueous phase is separated. The aqueous phase is again extracted with 2,2-difluoro-1-chloroethane and the combined organic phases are distilled as described in Example 1.1. Here also, the 4-methoxybenzylamine hydrochloride present in the aqueous phase can be converted back into free 4-methoxybenzylamine by addition of sodium hydroxide solution. After distillation, 4.93 g of 2,2-difluoro-N-(4-methoxybenzyl) ethanamine are obtained, which corresponds to a yield of 68%, based on reacted 4-methoxybenzylamine.

$^1$H NMR (CDCl$_3$): 7.22 (m, 2H), 6.87 (m, 2H), 5.83 (tt, 1H), 3.79 (s, 3H), 3.77 (2H), 2.94 (dt, 2H)

Example 5

Preparation of 2,2-difluoroethylamine (Stage (ii))

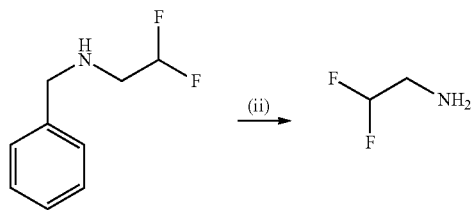

Example 5.1

An amount of 280 g (1.62 mol) of 2,2-difluoroethylbenzylamine is dissolved in 1260 ml of toluene and 7.0 g of 5% palladium-on-active charcoal (water-moistened, approximately 52% by weight of water) are added. After rendering inert, 6 bar of hydrogen are applied and the mixture is heated at 80° C. for 10 hours. After filtration of the catalyst, 2,2-difluoroethylamine is distilled. An amount of 109.8 g of 2,2-difluoroethylamine is obtained, which corresponds to a yield of 84%, based on the 2,2-difluoroethylbenzylamine used.

$^1$H NMR (CDCl$_3$): 5.5-5.9 (m, 1H), 2.94-3.1 (m, 2H), 1.26 (br m, NH$_2$)

The invention claimed is:

1. A process for the preparation of 2,2-difluoroethylamine of formula (I)

$$CHF_2CH_2NH_2 \quad (I)$$

and/or a salt thereof, comprising the stages (i) and (ii):

stage (i): reaction of 2,2-difluoro-1-haloethane of formula (II)

$$CHF_2\text{—}CH_2Hal \quad (II)$$

with a benzylamine compound of the formula (III)

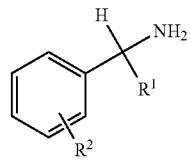 (III)

to give an N-benzyl-2,2-difluoroethanamine compound of formula (IV)

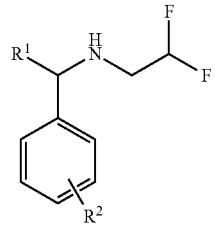 (IV)

in the presence of an acid scavenger, which comprises a compound which is able to inactivate and/or neutralize an acid;

in which, in formula (II),

Hal is chlorine, bromine or iodine, and, in the formulae (III) and (IV), $R^1$ is hydrogen or $C_1$-$C_{12}$-alkyl, and $R^2$ is hydrogen, halogen, $C_1$-$C_{12}$-alkyl or $C_1$-$C_6$-alkoxy; and stage (ii): catalytic hydrogenation of the N-benzyl-2,2-difluoroethanamine compound of the formula (IV) obtained in the stage (i), by which 2,2-difluoroethylamine of the formula (I) and/or a salt thereof is obtained.

2. The process according to claim 1, in which a portion of the benzylamine compound used acts as said acid scavenger, while another portion of the benzylamine compound of the formula (III) is reacted.

3. The process according to claim 1, in which, in stage (i), an organic or inorganic base is used as said acid scavenger.

4. The process according to claim 2, in which, in stage (i), the molar amount of 2,2-difluorohaloethane of the formula (II) used is greater than the sum of the molar amounts of acid scavenger and the benzylamine compound of the formula (III) which is reacted.

5. The process according to claim 1, in which stage (i) is carried out without solvent.

6. The process according to claim 1, in which stage (i) is carried out in the presence of a catalyst which is at least one selected from the group consisting of alkali metal bromides and iodides, ammonium bromide, ammonium iodide, tetraalkylammonium bromides, tetraalkyl-ammonium iodides, tetraalkylphosphonium halides, tetraarylphosphonium halides, tetrakis(dimethylamino)phosphonium bromide, tetrakis(diethylamino)phosphonium bromide, tetrakis(dipropylamino)phosphonium chloride, tetrakis(dipropylamino)phosphonium chloride, tetrakis(dipropylamino)phosphonium bromide, and bis(dimethylamino) [(1,3-dimethyl-imidazolidin-2-ylidene)amino]methylium bromide.

7. The process according to claim 1, in which, in the formulae (III) and (IV), $R^1$ and $R^2$ are each hydrogen and, in formula (II), Hal is chlorine.

8. A process for the preparation of an N-benzyl-2,2-difluoroethanamine compound of the formula (IV)

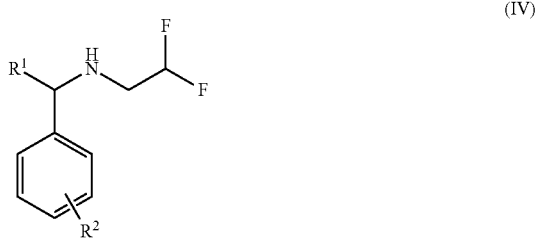

comprising reacting 2,2-difluoro-1-haloethane of formula (II)

$$CHF_2\text{—}CH_2Hal \quad (II),$$

with a benzylamine compound of the formula (III)

in the presence of an acid scavenger,
in which, in formula (II),
Hal is chlorine, bromine or iodine,
and, in the formulae (III) and (IV),
$R^1$ is hydrogen or $C_1$-$C_{12}$-alkyl, and
$R^2$ is hydrogen, halogen, $C_1$-$C_{12}$-alkyl or $C_1$-$C_6$-alkoxy.

9. The process according to claim 8,
in which, in the formulae (III) and (IV),
$R^1$ is hydrogen or $C_1$-$C_6$-alkyl, and
$R^2$ is hydrogen, fluorine, chlorine, bromine or iodine, $C_1$-$C_6$-alkyl or $C_1$-$C_3$-alkoxy or methoxy.

10. The process according to claim 8, in which, in the formulae (III) and (IV), $R^1$ and $R^2$ are each hydrogen and, in formula (II), Hal is chlorine.

11. The process according to claim 8, in which a portion of the benzylamine compound used acts as said acid scavenger, while another portion of the benzylamine compound of the formula (III) is reacted.

12. The process according to claim 8, in which an organic or inorganic base is used as said acid scavenger.

13. The process according to claim 8, in which the molar amount of 2,2-difluorohaloethane of the formula (II) used is greater than the sum of the molar amounts of said acid scavenger and the benzylamine compound of the formula (III) which is reacted.

14. The process according to claim 8, where said process is carried out without solvent.

15. The process according to claim 8, where the process is carried out in the presence of a catalyst which is at least one selected from the group consisting of alkali metal bromides and iodides, ammonium bromide, ammonium iodide, tetraalkylammonium bromides, tetraalkyl-ammonium iodides, tetraalkylphosphonium halides, tetraarylphosphonium halides, tetrakis(dimethylamino)phosphonium bromide, tetrakis(diethylamino)phosphonium bromide, tetrakis(dipropylamino)phosphonium chloride, tetrakis(dipropylamino) phosphonium chloride, tetrakis(dipropylamino) phosphonium bromide, and bis(dimethylamino)[(1,3-dimethyl-imidazolidin-2-ylidene)amino]methylium bromide.

* * * * *